United States Patent [19]

Granados Jarque et al.

[11] 4,178,450

[45] Dec. 11, 1979

[54] 2,5-DIMETHYL-BENZO(b) THIENE (3,2-f) MORPHAN AND PRECURSOR THEREOF

[75] Inventors: Ricardo Granados Jarque, Barcelona; Mercedes Alvarez Domingo, San Juan Despi; Juan Bosch Cartes, all of Barcelona; Cristóbal Martinez Roldán; Fernando Rabadán Peinado, both of Madrid, all of Spain

[73] Assignee: Laboratories Made, S. A., Madrid, Spain

[21] Appl. No.: 874,089

[22] Filed: Feb. 1, 1978

[30] Foreign Application Priority Data

Feb. 25, 1977 [ES] Spain ............................. 456281

[51] Int. Cl.² .................. C07D 495/08; C07D 409/06
[52] U.S. Cl. ..................................... 546/63; 424/263; 424/267; 546/274; 549/49
[58] Field of Search .................. 260/DIG. 13, 293.54, 260/294.8 C; 424/263, 267; 546/63, 274

[56] References Cited

U.S. PATENT DOCUMENTS 3,382,249  5/1968  Albertson ..................... 260/293.54

OTHER PUBLICATIONS

Chemical Abstracts, 85:21169g (1976) [Alvarez, M. et al., An. Quim. 1975, 71(9–10), 807–9].
Bosch, J., et al., J. Het. Chem., 12, 651–654 (1975).
Perry, R., et al., J. Med. Chem., 10, 1184–86 (1967).

*Primary Examiner*—John M. Ford
*Assistant Examiner*—Richard A. Schwartz
*Attorney, Agent, or Firm*—Ladas, Parry, Von Gehr, Goldsmith & Deschamps

[57] ABSTRACT

2,5-dimethyl-benzo [b] thiene [3,2-f] morphan and 2-(2-benzo [b] thienyl-methyl)-1,4-dimethyl-1,2,3,6-tetrahydropyridine or their pharmacologically acceptable acid addition salts are useful as analgesic agents.

3 Claims, No Drawings

2,5-DIMETHYL-BENZO(b) THIENE (3,1-f) MORPHAN AND PRECURSOR THEREOF

This invention relates to obtaining 2,5-dimethyl-benzo[b]thiene[3,2-f]morphan (I), an intermediate for its preparation 2-(2-benzo[b]thienylmethyl)-1,4-dimethyl-1,2,3,6-tetrahydropyridine (II) and the addition salts thereof with pharmacologically acceptable acids, for example hydrochlorides.

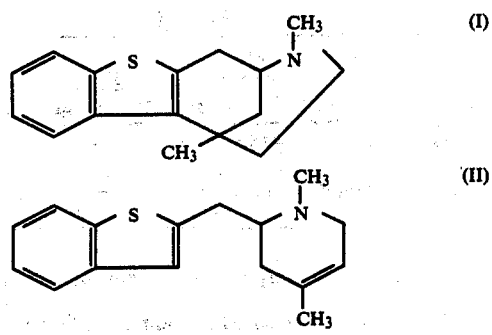

The cited compounds are new substances of possible interest as analgesics, and are prepared according to the following reaction sequence:

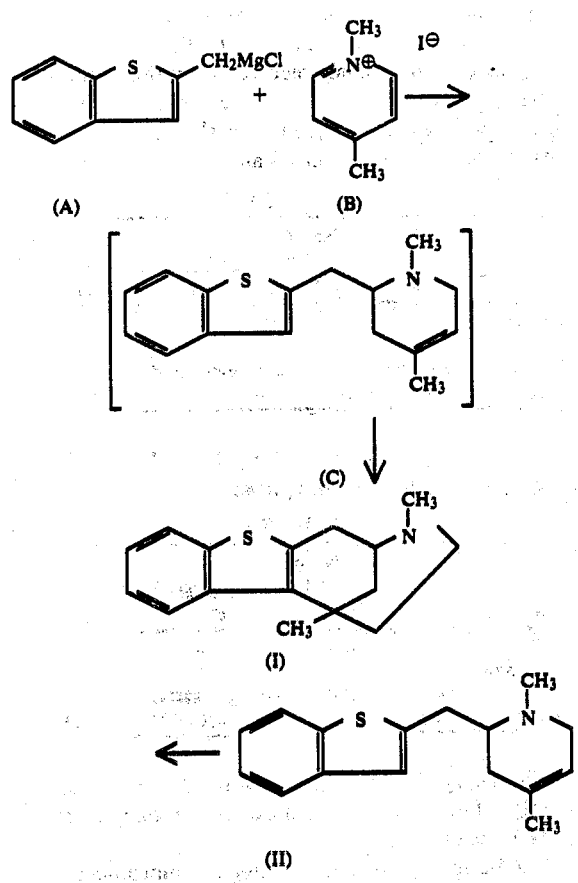

In the first part of the process, 2-chloromethyl-benzo[b]thiophene magnesiane (A) is obtained in conditions of high dilution and in inert atmosphere, and is made to react at reflux temperature with 1,4-dimethyl-pyridinium iodide (B) in anhydrous ether, thus obtaining the unstable 2-(2-benzo-[b]thienylmethyl-1,4-dimethyl-1,2-dihydropyridine (C) intermediate.

Said intermediate, without subsequent purification, is reduced in basic medium with sodium borohydride in aqueous methanolic solution. The organic layer provides a mixture from which isolation can be made, by distillation, of the compound II, 2-(2-benzo[b]thienylmethyl)-1,4-dimethyl-1,2,3,6-tetrahydropyridine, from which the corresponding hydrochloride is obtained.

In a second step of the process the previously obtained raw mixture is heated at 135° C. for 14 hours in a strong acid, such as for example 48% aqueous hydrobromic acid. It is poured over ice and water, alkalinized with ammonium hydroxide and extracted with ether, thus producing the 2,5-dimethyl-benzo[b]thiene [3,2-f]morphan (I).

The following examples are given only as illustrations, and must not be considered in any way limitative of the scope of the invention.

EXAMPLE 1.

Obtaining 2-(2-benzo[b]thienylmethyl)-1,4-dimethyl-1,2,3,6-tetrahydropyridine. (II).

To obtain 2-benzo[b]thienylmethylmagnesium chloride use has been made of the "modified cyclic reactor" embodying a continuous flow column provided with a separation funnel, coolant and reaction flask.

The reactor column is packed with 70 g of magnesium in chips alternated with thin layers of mercuric chloride, and is covered with a saturated solution of mercuric chloride in anhydrous ether. Following 48 hours of repose, 250 ml of anhydrous ether are introduced in the flask and are made to reflux for 2 hours. The flask is substituted by another equipped for mechanical stirring in which 49.3 g of 1,4-dimethyl-pyridinium iodide are introduced in suspension with 500 ml of anhydrous ether. 36 g of 2-chloromethylbenzo[b]-thiophene dissolved in 400 ml of anhydrous ether are placed in a separation funnel, some ml of the halogenide solution are added to the magnesium column and when it is seen that the reaction has begun the flask is heated to reflux temperature, the addition continuing slowly for 6 hours. During the entire process a nitrogen atmosphere is maintained in the system.

When addition is concluded reflux is continued for 4 hours; the resulting ether solution is poured over 500 ml of aqueous solution of ammonium chloride and ice; the mixture is alkalinized with ammonium hydroxide and is extracted with ether. The ether solution is extracted with 10% hydrochloric acid; the aqueous layer is alkalinized with concentrated ammonium hydroxide and is extracted with ether. The ether extract dried with magnesium sulfate and evaporated provides 42.5 g of the unstable 2-(2-benzo[b]thienylmethyl)-1,4-dimethyl-1,2-dihydropyridine intermediate. To the 42.5 g of said intermediate dissolved in 275 ml of methanol are added 166 ml of 1 N sodium hydroxide and 6.8 g of boron tetrahydride and sodium. The mixture is heated at reflux temperature and is stirred for 12 hours. The resulting product is extracted with ether and is dried with magnesium sulfate. Once the ether has evaporated, 22.6 g of a tetrahydropyridine mixture are obtained. The yield of the process is 45%. From said mixture the 2-(2-benzo[b]thienylmethyl)-1,4-dimethyl-1,2,3,6-tetrahydropyridine (II) can be isolated by distillation (b.p. 113–130/0.03 mm Hg) followed by crystallization of the corresponding hydrochloride. An analytical sample recrystallized from ether-acetone has a melting point of 214°–18° C.

Calculated analysis for $C_{16}H_{20}ClNS$: C, 65.40; H, 6.85; N, 4.76; S, 10.91; Cl, 12.06.

Found: C, 65.49; H, 6.88; N, 4.49; S, 10.70; Cl. 12.15.

EXAMPLE 2.

Obtaining 2,5-dimethyl-benzo[b]thiene-[3,2-f]morphan (I).

A solution of 6.5 g of the tetrahydropyridines mixture previously obtained in 87.3 ml of 48% aqueous hydrobromic acid is heated at 130°–5° C. for 14 hours. The mixture is allowed to cool, is poured over ice and water, is alkalinized with ammonium hydroxide and is extracted with ether. The ether extract, dried with magnesium sulfate and evaporated, provides 5.47 g of an oil which is purified by distillation, the distilling fraction collecting between 125°–270° C./0.08 mm Hg. Yield is 68%. The hydrochloride is precipitated and is purified by recrystallization from ether-acetone thus obtaining a solid having a melting point of 135°–8° C.

Calculated analysis for: $C_{16}H_{20}ClNS \cdot H_2O$: C, 61.65; H, 7.09; N, 4.49. Found: C, 61.34; H, 7.29; N, 4.31.

PHARMACOLOGY OF THE PRODUCTS OF THE INVENTION

Products

I-2,5-dimethyl-benzo[b]thiene[3,2-f]morphan.

II-2-(2-benzo[b]thienylmethyl-1,4-dimethyl-1,2,3,6-tetrahydropyridine.

These are products of analgesic activity. Their activity has been studied in comparison with that of dextropropoxyphene.

A—ACUTE TOXICITY Acute toxicity studies have been made in I.C.R. Swiss albino mice of both sexes of a weight of $30 \pm 2$ g, kept without food for 24 hours prior to the experiment. Ambient temperature and relative humidity were held constant. The products were administered intraperitoneally, with the number of deaths noted 48 hours from the moment of treatment. Calculation of the lethal dose 50 ($LD_{50}$) was made by the Litchfield-Wilcoxon test. The following are the results obtained:

TABLE I

| Product | $LD_{50}$ (mg/kg) |
|---|---|
| I | 90.8 |
| II | 916.3 |
| Dextropropoxyphene | 140 |

B—ANALGESIC ACTIVITY

1. Thermal analgesia

The thermal analgesic effect has been studied in I.C.R. Swiss albino mice. The 55° C. "hot plate" technique was used. Batches of 10 mice were made. The products in study were administered intraperitoneally and after 30 minutes the mice were placed on the hot plate and note was made, in seconds, of the time it took them to jump. Batches were made of control animals injected only with distilled water. The results are shown in Tables 2 and 3.

TABLE II

| Treatment | Dose | Jumping time in sec. $\bar{x} \pm$ S.E.M. | Significance of Diff. Dextroprop. | Control |
|---|---|---|---|---|
| Control | — | $30.9 \pm 5.016$ | — | — |
| Dextropropoxyphene | 25mg/kg | $70.8 \pm 13.592$ | — | $p<0.02$ |
| Prod. I | 25mg/kg | $48.9 \pm 8.956$ | N.S. | N.S. |

Product I lacks any thermal analgesic activity.

TABLE III

| Treatment | Dose | Jumping time in sec. $\bar{x} \pm$ S.E.M. | Significance of Diff. Dextroprop. | Control |
|---|---|---|---|---|
| Control | — | $48.8 \pm 5.033$ | — | — |
| Dextropropoxyphene | 50mg/kg | $91.3 \pm 7.894$ | — | $p<0.00005$ |
| Prod. II | 50mg/kg | $63 \pm 8.368$ | $p<0.05$ | N.S. |

Product II lacks any thermal analgesic activity.

2. Chemical analgesia The analgesic effect has been studied in I.C.R. Swiss albino mice, employing the acetic acid writhing technique. Batches of 10 mice were made.

The products studied were administered intraperitoneally, and after 30 minutes the mice were injected intraperitoneally with 0.25 ml of 1% acetic acid. A batch of control animals received only the acetic acid. Note was made of the number of writhes in each mouse 20 minutes following injection of the acetic acid. The results are shown in Tables 4 and 5.

TABLE IV

| Treatment | Dose | No. of writhes $\bar{x} \pm$ S.E.M. | Significance of Differences Control | Dextroprop. |
|---|---|---|---|---|
| Control | — | $122.1 \pm 9.15$ | — | — |
| Dextropropoxyphene | 30mg/kg | $24 \pm 6.03$ | $p<0.00005$ | — |
| Prod. I | 30mg/kg | $44.3 \pm 6.14$ | $p<0.00005$ | $p<0.05$ |

Product I has analgesic activity, but of lesser intensity than that of dextropropoxyphene.

TABLE V

| Treatment | Dose | No. of writhes $\bar{x} \pm$ S.E.M. | Significance of Diff. Control | Dextroprop. |
|---|---|---|---|---|
| Control | — | $109.9 \pm 6.362$ | — | — |
| Dextropropoxyphene | 25mg/kg | $27.8 \pm 8.365$ | $p<0.00005$ | — |
| Prod. II | 25mg/kg | $41.2 \pm 6.024$ | $p<0.00005$ | N.S. |

The analgesic activity of Product II is not significantly different from that of dextropropoxyphene.

What is claimed:

1. 2,5-dimethyl-benzo[b]thiene[3,2-f]morphan or 2-(2-benzo[b]thienylmethyl)-1,4-dimethyl-1,2,3,6-tetrahydropyridine or one of their pharmacologically acceptable acid addition salts.

2. The compound defined in claim 1 which is 2,5-dimethyl-benzo[b]thiene[3,2-f]morphan of the formula:

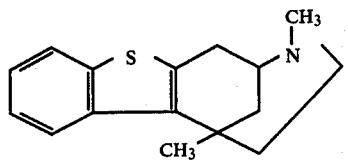
or a pharmacologically acceptable acid addition salt thereof.
3. The compound defined in claim 1 which is 2-(2-benzo[b]thienylmethyl)-1,4-dimethyl-1,2,3,6-tetrahydropyridine of the formula:
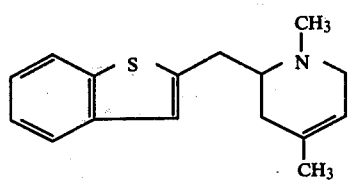
or a pharmacologically acceptable acid addition salt thereof.
* * * * *